United States Patent
Yoshimi et al.

[19]

[11] Patent Number: 6,030,388
[45] Date of Patent: *Feb. 29, 2000

[54] TOP TIGHTENING BONE FIXATION APPARATUS

[75] Inventors: Shunshiro Yoshimi, La Quinta; Rick B. Delamarter, Los Angeles; Angela Melton, Palm Desert; Mike Stednitz, Indio, all of Calif.

[73] Assignee: Alphatech Manufacturing, Inc., Palm Desert, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/695,318

[22] Filed: Aug. 9, 1996

[51] Int. Cl.⁷ .................................................. A61B 17/70
[52] U.S. Cl. .............................................. 606/61; 606/72
[58] Field of Search ................................. 606/60, 61, 72, 606/73

[56] References Cited

U.S. PATENT DOCUMENTS

| | | | |
|---|---|---|---|
| 4,946,458 | 8/1990 | Harms et al. | 606/61 |
| 5,403,314 | 4/1995 | Currier | 606/61 |
| 5,474,555 | 12/1995 | Puno et al. | 606/61 |
| 5,501,684 | 3/1996 | Schlapfer et al. | 606/61 |
| 5,527,314 | 6/1996 | Brumfield et al. | 606/72 |

FOREIGN PATENT DOCUMENTS

92 15 561   1/1993   Germany .

*Primary Examiner*—Michael Buiz
*Assistant Examiner*—Daphna Shai
*Attorney, Agent, or Firm*—Knobbe, Martens Olson & Bear, LLP

[57] ABSTRACT

The present invention includes a bone fixation apparatus comprising a bone fixation element, a linking member, and a coupling member. The coupling member has a first channel for receiving a portion of the bone fixation element and a second channel for receiving a portion of the linking member. The first and second channels are configured within the coupling member so as to allow communication of a securing force from the bone fixation element to the linking member such that the bone fixation element is rigidly secured with respect to the linking member. The bone fixation element may incorporate a conical load bearing surface which contacts the linking member through a third channel in the coupling member. Upward axial movement provided by nut tightening forces the load bearing surface of the bone fixation element against the linking member, thereby securing both within the coupling member.

12 Claims, 5 Drawing Sheets

TOP TIGHTENING BONE FIXATION APPARATUS

CROSS REFERENCE TO RELATED APPLICATION

FIELD OF THE INVENTION

This invention relates to prosthetic devices used in bone fixation systems, such as those used to treat degenerative and trauma related spinal deformities. Specifically, this invention relates to fixation rod and bone screw/hook systems for stabilizing multiple vertebra.

BACKGROUND OF THE INVENTION

A wide variety of spinal fixation systems are currently in use by orthopedic surgeons. These various systems are widely used to help safely secure and stabilize the spine to correct deformities. In addition, spinal implant systems can aid in a healing process from trauma, or assist in the treatment of degenerative conditions. These types of implants are designed to resist post operative fatigue and failure until bone fusion occurs.

In general, two or more bone screws and/or hooks are secured to the vertebra to be stabilized. After installation, the screws or hooks extend outward roughly perpendicular to the spinal column. They are then coupled to a spinal fixation rod which is placed roughly parallel to the spinal column, thus restricting the movement of the stabilized vertebra. In most applications, two spinal fixation rods are provided, each coupled to bone screws or hooks provided on both sides of the spinal column. The two spinal rods are often attached to one another with transverse connecting pieces.

It can be appreciated that the coupling means securing the bone screws or hooks to the spinal fixation rod is important to both the effectiveness and ease of installation of such spinal fixation systems. Various coupling means have been used. In some systems, the bone screw or hook incorporates a "Y" shaped head containing a lateral fixation rod engagement groove. An eyebolt is provided which fits between the posts forming the "Y", and a nut is tightened onto the eyebolt which holds the "Y" shaped head against the fixation rod in the lateral engagement groove. This type of coupling means is exemplified in U.S. Pat. No. 5,246,442 to Ashman et al.

Eyebolt type coupling systems have several disadvantages. The eyebolt may score the fixation rod, leading to premature failure. Also, the surgeon is required to bend the rod to conform to the lordotic (concave) or kyphotic (convex) curves in the surgical area to position the rod engaging portion of the screw or hook exactly perpendicular to the rod. Furthermore, because such eyebolts attach to the spinal rod in a "side-tightening" manner, access to the nut during surgery is limited, making the process of tightening the nut laborious and time consuming.

In response to these problems, various forms of adjustable and "top tightening" coupler systems have been devised. For example, U.S. Pat. No. 5,047,029 to Aebi, et al. describes a coupling device which incorporates a threaded compressible collet which clamps down on the shaft of a bone screw as the collet is drawn into an eye by turning a nut threaded onto the collet. U.S. Pat. Nos. 5,129,899 to Small et al. and 5,092,893 to Smith both describe bone screws incorporating upper threaded portions that extend through a slot in a plate, wherein the plate acts as a fixation device. The screw is secured directly to the plate by threading a top tightening nut onto the upper portion of the bone screw which protrudes through the slot in the plate. Although they are improvements over the side tightening eyebolt type coupling, these systems remain imperfect. For example, angular adjustability is not appreciably present in either the Small or Smith systems, and the Aebi device requires independent attachment to the rod and the bone screw.

Accordingly, it would be beneficial to provide a coupling device for a bone fixation system incorporating the benefits of wide angular adjustability as well as allowing single nut top access tightening.

SUMMARY OF THE INVENTION

The present invention includes a bone fixation apparatus comprising a bone fixation element including a bone engagement portion which may comprise a threaded screw or hook, a linking member adapted to interconnect a plurality of bone fixation elements, and a coupling member having a first channel for receiving a portion of the bone fixation element and a second channel for receiving a portion of the linking member. The channels are oriented within the coupling member such that the central longitudinal axes of the first and second channels are offset with respect to one another. Furthermore, the first and second channels are configured within the coupling member so as to provide for communication of a securing force between the bone fixation element and the linking member such that the bone fixation element is rigidly secured with respect to the linking member.

In preferred embodiments, the coupling member contains a third channel connecting the first and second channels. In these embodiments, this third channel allows communication of the securing force from the bone fixation element to the linking member. Preferably, the longitudinal axes of the first, second, and third channels are mutually perpendicular, and the longitudinal axis of the third channel intersects the longitudinal axes of the first and second channels.

The lateral offset between the linking member channel and the bone fixation element channel may be varied. When the lateral offset is sufficiently large, a load transfer member is slidably retained inside the third channel so as to allow communication of the securing force from the bone fixation element to the linking member. When the lateral offset is sufficiently small, the third channel comprises a window defined by an intersecting region of the first channel and second channel.

In particularly preferred embodiments, the bone fixation element includes a conical load bearing surface which either contacts the load transfer member which in turn contacts the linking member, or contacts the linking member directly. Upward axial movement forces the load bearing surface of the bone fixation element against the linking member, thereby securing them both within the coupling member. Upward axial motion of the bone fixation element is preferably provided by tightening a nut threaded onto an upper threaded portion of the bone fixation element.

DETAILED DESCRIPTION OF THE PREFERRED EMBODIMENTS

Figure 1:
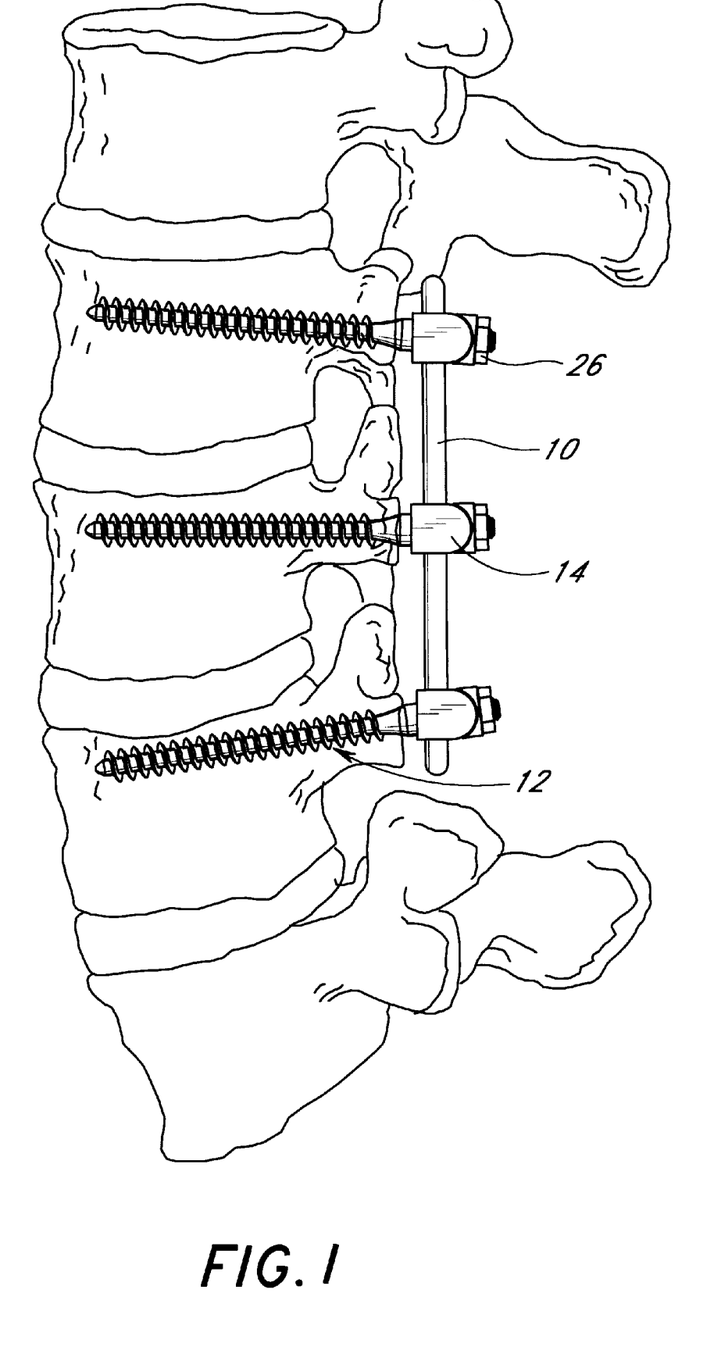
FIG. 1 illustrates a spinal fixation construct according to the present invention, showing three fixation systems secured to three separate vertebra of a spinal column.

By way of introduction, reference is made to FIG. 1, which illustrates a vertebral fixation construct applied to a human spinal column which incorporates the bone fixation system of the present invention. Such constructs have found prevalent use in stabilizing the vertebra of a human spinal column. Accordingly, the bone fixation system described herein is described-with reference to that particular use. However, it can be appreciated that stabilization of any multi-bone structure may be accomplished using the present invention, and such other uses are also contemplated.

The construct of FIG. 1 is formed with three bone fixation elements threaded into three separate vertebra. Also provided is a linking member 10, comprising in this case a fixation rod with circular cross section, and coupling members 14 for securing bone fixation elements 12 to the spinal fixation rod. It may be noted in connection with FIG. 1 that the bone fixation elements 12 are not necessarily oriented perpendicular to the linking member 10. Furthermore, a single nut 26, which approximately faces the surgeon during the construct installation procedure is used to secure the bone fixation elements 12 to the linking member 10. The attainment of these beneficial aspects of fixation constructs using the fixation system of the present invention is described in detail below.

Figure 2:
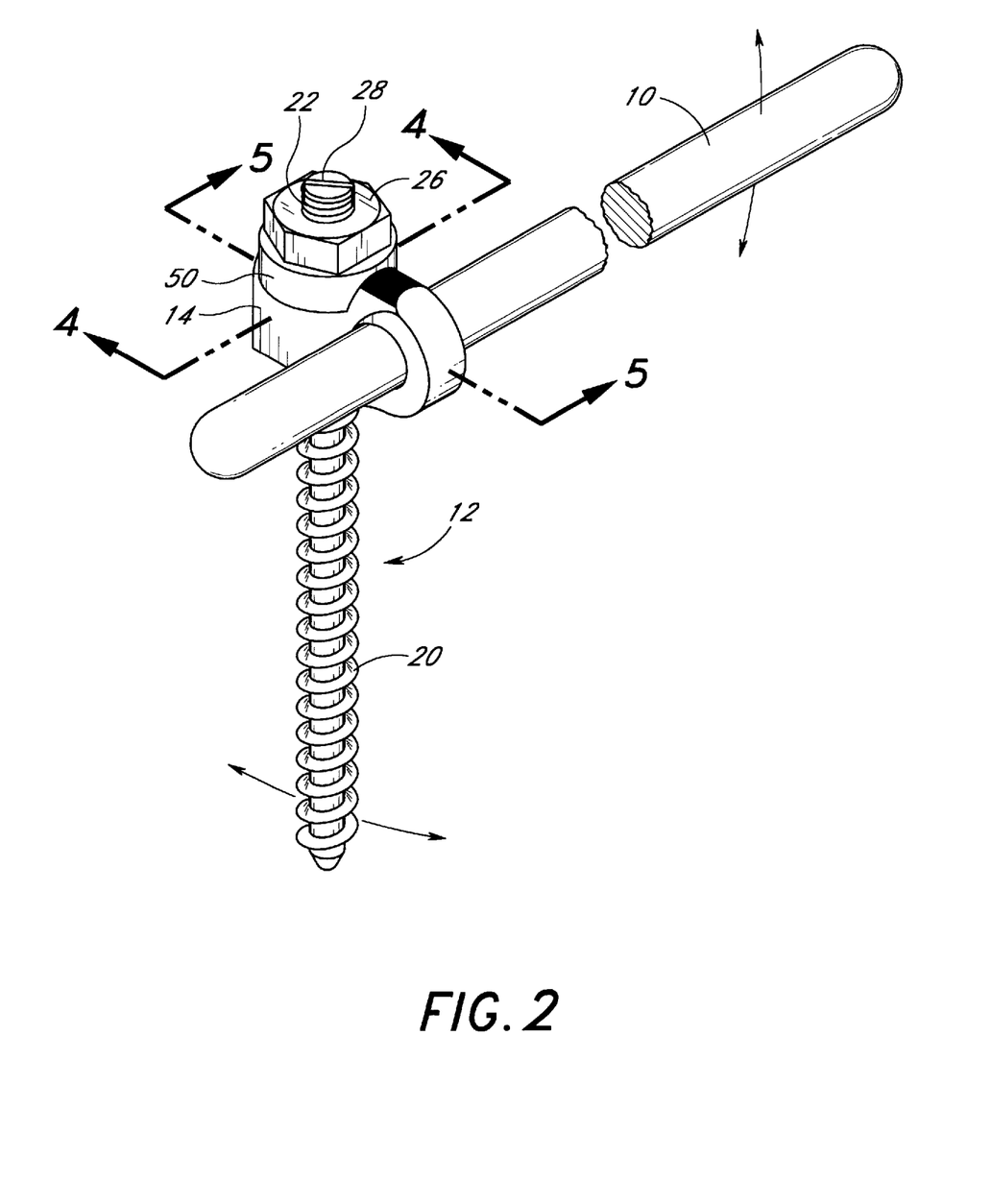
FIG. 2 is a perspective view of the fixation system of the present invention, showing the fixation rod, bone engagement element, and coupling member.
Figure 3:
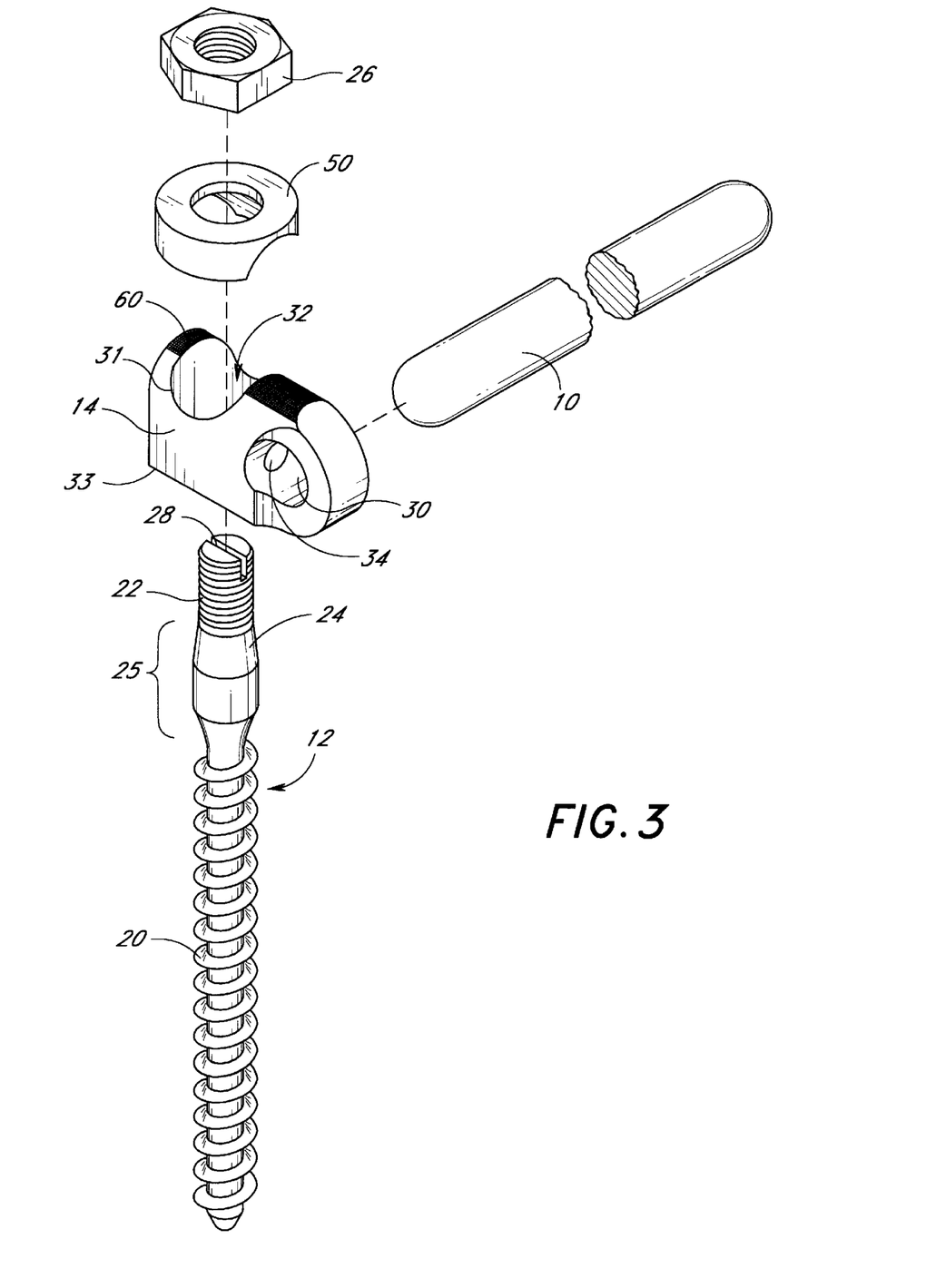
FIG. 3 is an exploded perspective view of the fixation system of FIG. 2, illustrating the nut and collar which engages the threaded-portion of the bone fixation element, as well as the load bearing surface of the bone fixation element.

A perspective and an exploded perspective view of a bone fixation system according to the present invention are provided in FIGS. 2 and 3 respectively. The system illustrated in FIGS. 2 and 3 comprises a linking member 10, preferably a fixation rod, a bone fixation element 12, and a coupling member 14. In use, both the rod 10 and the bone fixation element 12 are rigidly secured to the coupling member 14, via the mechanisms explained in detail herein.

The fixation rod 10 may vary greatly in length depending on the number of vertebra to be stabilized and the number of bone fixation elements to be attached along its length. Typically, the linking member 10 has a solid circular cross section, and has diameter of approximately ¼ in.

Referring now to FIG. 2, the bone fixation element 12 includes a lower bone engagement portion 20. This portion 20 may comprise any suitable means for attachment to vertebra or other bone. In the illustrated preferred embodiment, this portion 20 is a threaded screw. Alternatively, the bone engagement portion may comprise various styles of vertebral hooks such as pedicle or lamina hooks which are also well known to those in the art.

Refering now to FIG. 3, above the bone engagement portion 20 is an expanded shoulder portion 25 comprising a load bearing surface 24 which has a tapered conical cross section such that the diameter of the bone fixation element 12 decreases as the bone fixation element 12 extends upward from the widest part of the expanded shoulder region 25.

Above the expanded shoulder region 25, the upper end of the bone fixation element 12 opposite the bone engagement portion 20 comprises a threaded portion 22 which is adapted to receive a nut 26.

In one preferred embodiment, the threaded portion 22 having a diameter of approximately 0.23 inches extends downward from the top of the bone fixation element approximately 0.3 inches. The load bearing surface 24 comprising the upper portion of the expanded shoulder region 25 then tapers outward at approximately a 13 degree angle for a distance of approximately 0.16 inches, resulting in an expanded diameter of approximately 0.282 inches. The expanded shoulder portion 25 of the bone fixation element 12 then continues to extend downward at the 0.282 in. diameter for approximately 0.213 inches. The remaining lower portion of the bone fixation element 12 is threaded in a manner suitable for securement into vertebra or other bone.

A preferred coupling member 14, illustrated in both FIGS. 2 and 3, is provided with three channels, two of which extend through the coupling member, with the third extending within the coupling member 14 so as to intersect with and connect the other two channels. Preferably, the central longitudinal axes of the three channels are orthogonal. More particularly, with reference to FIG. 3, it is seen that a first channel 30 defines a fixation rod channel extending approximately horizontally through coupling member 14. Channel 30 is adapted to allow slidable insertion of the linking member 10 (in this case a rod) with a relatively snug fit that is nevertheless loose enough so that the linking member 10 is manually slidable within coupling member 14. Although various cross sectional area configurations may be employed, both the rod 10 and channel 30 preferably have circular transverse cross sections to allow free rotation of the coupling member 14 about the longitudinal axis of the rod 10 prior to final securement.

The coupling member 14 is further provided with a second channel 32, defining a bone fixation element channel, which extends approximately vertically through the coupling member 14. The mutually perpendicular central longitudinal axes of the channels 30,32 are laterally spaced apart, or offset, from one another such that they do not intersect. This channel 32 is adapted to slidably accept insertion of the top threaded portion 22 of the bone fixation element 12.

At the top of the coupling member 14, the exit opening of the channel 32 forms an elongated oval slot 31, with a major axis parallel to the longitudinal axis of the fixation rod channel 30, and a minor axis perpendicular to the longitudinal axis of the fixation rod channel 30. The overall dimensions of this upper opening of the bone fixation element channel 32 are such that the major axis is approximately 1.5 times larger than the minor axis, and the minor axis measures approximately the same as the diameter of the threaded portion 22 of the bone fixation element 12.

At the bottom of the coupling member 14, where the vertical channel 32 exits the bottom of the coupling member 14, the exit opening also forms an elongated slot 33 with identical orientation as the top slot 31, and with a major axis measuring 1.5 times larger than the minor axis. However, as can be seen by reference to FIG. 4, the dimensions of the transverse cross section of channel 32 are larger at the bottom of the coupling member 14 than the dimensions of the transverse cross section of the channel 32 at the top of the coupling member 14. The dimension of the minor axis of the transverse cross section of channel 32 at the bottom of the coupling member 14 is approximately equal to the diameter of bone fixation element 12 at the widest section of the expanded shoulder portion 25 below the outward taper which forms the load bearing surface 24. In particular, it is also noted that the transverse cross section of the bone fixation element channel 32 necks down to a smaller approximately circular shape, with diameter slightly greater than the diameter of the threaded portion 22 of the bone fixation element 12, but less than the diameter of the bone fixation element 12 at the widest section of the expanded shoulder portion 25 which is located below the outward taper forming the load bearing surface 24. The longitudinal cross section of this channel 32 is therefore approximately hourglass shaped, with a larger bottom than top.

In addition to the two channels described above, FIG. 3 illustrates a third channel 34, defining a load transfer channel which is also positioned approximately horizontally in the coupling member 14. This load transfer channel 34 extends between and joins the other two channels 30,32. The longitudinal axis of the load transfer channel 34 is perpendicular to both the other channels, and is situated such that it intersects the longitudinal axes of both the bone fixation element channel 32 and the fixation rod channel 30. This channel 34 allows for a communication of forces between the channel 30 for the spinal fixation rod 10, and the channel 32 for the bone fixation element 12. This load transfer channel 34 is preferably of smaller diameter than both the bone fixation element channel 32 and the spinal rod channel 30. Preferably, it intersects the bone fixation element channel 32 approximately at its small diameter neck 35, and intersects the spinal rod channel 30 at approximately its longitudinal midpoint where the two channels 30,32 come closest to intersecting.

Figure 5A:
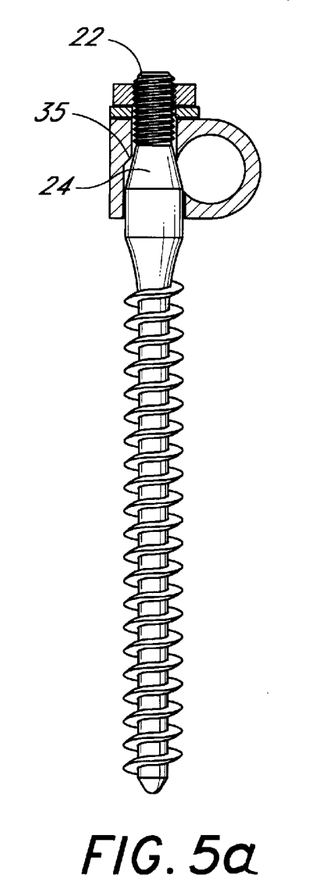
FIG. 5a is a partial cutaway view of a portion of the fixation system of the present invention, taken along lines 5—5 of the fixation system of FIG. 2.

One preferred embodiment of the invention is shown in FIG. 5a, wherein the load transfer channel 34 is defined as a window between intersecting surfaces of channels 30 and 32. More particularly, when the fixation rod channel 30 and the bone fixation element channel 32 are laterally spaced sufficiently close that they intersect each other, the load transfer channel 34 comprises a window that is created naturally at the intersection location of the other two channels 30,32. In this case, no additional cylindrical bore or tunnel need be machined into the coupling member 14, because the channels 30,32 will automatically create a connection between themselves which is defined by their region of intersection.

Figure 5B:
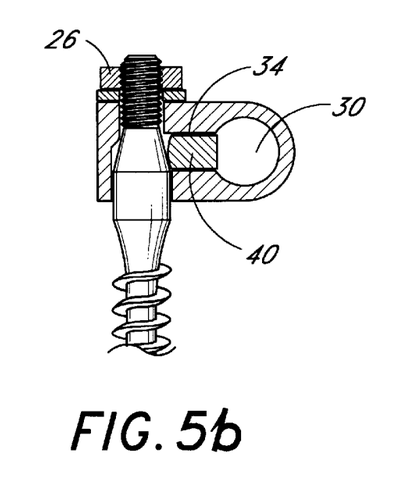
FIG. 5b is a cutaway view of the fixation system of the present invention along lines 5—5 of FIG. 2, wherein the fixation system of FIG. 2 incorporates a lateral offset type coupling member.

In another preferred embodiment, illustrated in FIG. 5b, the bone fixation element channel 32 may be laterally spaced a long distance from the fixation rod channel 30 relative to the respective channel diameters. In this configuration, the load transfer channel 34 connecting them will be a preferably cylindrical bore or tunnel beginning at the fixation rod channel 30, and ending at the bone fixation element channel 32. The diameter of this bore is preferably approximately ½ to ¾ of the diameter of the spinal rod channel 30 and of the bone fixation channel 32.

To accomplish load transfer when channel 30 and channel 32 are laterally separated in this manner, a load transfer member 40, comprising a rod or pin is retained within the load transfer channel so as to be longitudinally slidable within the load transfer channel 34. The load transfer member 40 has a length that allows contact of one end of the load transfer member 40 with a surface of the fixation rod 10, while the other end of the member 40 simultaneously is in contact with the load transfer surface 24 of the bone fixation element 12. The mechanism of load transfer via the load transfer member 40 is discussed in greater detail below.

These three fundamental elements, a linking member 10, a bone fixation element 12, and a load transferring coupling member 14 work together in the following manner to create an effective and easy to use fixation system.

As is shown and was briefly described above with reference to FIG. 1, several bone fixation elements 12 are initially attached (via screw threads or hooks, or a combination of both) to several vertebra to be stabilized. When a threaded screw type bone engagement portion is provided, the bone fixation element 12 incorporates means for threading the screw into the bone such as a screwdriver slot 28 in the top of the bone fixation element 12. Other alternative driving means may be employed, such as a hexagonal recess for an allen wrench in the top surface of the bone fixation element 12, or a hexagonal wrench attachment point integrally formed on the bone fixation element 12 at the lower region of the expanded shoulder portion 25.

A number of coupling members 14 equal to the number of attached bone fixation elements 12 are slid over a spinal fixation rod of suitable length. The fixation rod 10 is placed adjacent to the spinal column and the coupling members 14 are manually adjusted along its length to approximately match the positions of the attached bone fixation elements 12.

Several aspects of the present invention can now be appreciated. First, the position of the several bone fixation elements 12 may not readily allow them all to be placed adjacent to a rigid, straight metal fixation rod 10. Some bone fixation elements 12 will usually be laterally spaced away from the fixation rod 10. Previously, the surgeon had to bend the rod 10 so that its position along the spine was made to closely correspond to the previous placement of the bone fixation elements 12.

The present invention allows the surgeon to choose from an assortment of coupling members 14 that have varying lateral distances between the spinal rod channel 30 and the bone engagement channel 32. Referring again to FIGS. 5a and 5b, presently preferred embodiments include coupling members wherein the rod channel 30 and the bone fixation element channel 32 intersect slightly, and naturally create a load transfer channel 34 (termed a "no offset" coupling member), and also wherein the edges of the two channels are separated by either 3 mm or 6 mm (termed a "lateral offset" connector). If the surgeon can choose during a surgical procedure from such an assortment of differing lateral offset channel coupling members 14, required bending of the fixation rod 10 can be minimized or eliminated entirely.

Figure 4:
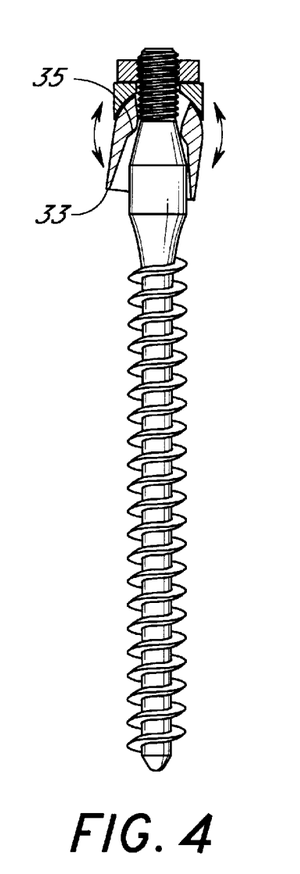
FIG. 4 is a partial cutaway view of the fixation system of the present invention taken along lines 4—4 of FIG. 2.

Furthermore, as was described above with reference to FIG. 1, the bone fixation elements 12 may not extend outward in a direction which is exactly perpendicular to the placement of the fixation rod 10. Because of the slidable fit of the rod 10 within the rod channel 30 of the coupling member 14 prior to tightening, the bone fixation element channel 32 can be oriented at various angles in a plane approximately perpendicular to the sagittal plane. Furthermore, as is shown in FIG. 4, the hourglass shape of the longitudinal cross section of the bone fixation element channel 32 allows the bone fixation element 12 to be inserted into its channel 32 at various angles in the sagittal plane. This freedom enhances the ease of fixation rod 10 installation, especially where threaded Schanz screw type bone engagement portions 20 are used, as the orientation or position of this type of bone fixation element cannot be changed once it is screwed into bone. As was true with bone fixation elements laterally offset from the linking member, angulation in the saggital plane can eliminate the time consuming need to contour or bend the linking member. As will be described in more detail below with reference to FIGS. 6a, 6b, 7a, and 7b, toothed or serrated mating surfaces allow solid securement even at non-perpendicular orientations.

Referring again to FIGS. 4, 5a, and 5b, the relatively small diameter of the neck section 35 of the bone fixation element channel 32 prevents the bone fixation element 12 from further insertion into the channel 32 once the outward tapering region comprising the load bearing surface 24 reaches this neck area of the channel 32. In this configuration, the top threaded region 22 of the bone fixation element 12 extends up through the top of the coupling member 14, and the load bearing surface 24 of the bone fixation element 12 is adjacent to the load transfer channel 34 which connects the bone fixation element channel 32 with the fixation rod channel 30.

In the "no offset" configuration described above and illustrated in FIG. 5a, the load bearing surface 24 of the bone fixation element 12 directly contacts the surface of the fixation rod 10 after both are inserted into their respective channels 30,32. If a lateral offset type coupling member 14 is used as illustrated in FIG. 5b, the rod 10 edge and the load bearing surface 24 of the bone fixation element are laterally separated. However, in the lateral offset embodiment, the load transfer member 40 is slidably captured in the load transfer channel 34, with length approximately equal to the load transfer channel 34, such that the load bearing surface 24 contacts the end of the load transfer pin 40 adjacent to the bone fixation element channel 34, thereby forcing the other end of the load transfer pin 40 which is adjacent to the fixation rod channel 30 to contact the surface of the fixation rod 10. Although not required for efficacy, it is preferable for the end of the load transfer pin 40 which is in contact with the load transfer surface 24 to be slightly convex, whereas the end of the load transfer pin 40 adjacent to the fixation rod 10 is preferably flat.

The means by which the rod 10 and the bone engaging element 12 are secured to each other and to the coupling member 14 may be described by reference to FIG. 4. In particular, it may be recalled that the hourglass shape of the bone fixation element channel 32 allows the threaded portion 22 of the bone engaging element 12 to extend up through the top of its channel 32 with an orientation that is not necessarily perpendicular to the fixation rod 10. To facilitate secure coupling in the presence of such a non-perpendicular orientation, a collar member 50 is provided with a round, concave bottom surface adapted to fit tightly over the top of the coupling member 14, which is provided with a substantially matching round, convex top surface. The collar member 50 has a flat top surface, such that a flat surface normal to the extension of the threaded portion 22 of the bone fixation element 12 is present for the nut 26 to tighten against.

As the nut 26 is tightened down onto the threaded portion 22 of the bone fixation element 12, the bone fixation element 12 is drawn further upward into its channel 32 in the coupling member 14. As it is drawn upward, the load bearing surface 24 presses directly against the fixation rod 10 in the "no offset" configuration, or against the load transfer member 40, in the lateral offset configurations. In both embodiments, the increasing diameter of the bone fixation element 12 at the load bearing surface forces both the rod 10, and the bone fixation element 12 against opposite sides of their respective channels as the bone fixation element 12 is forced further into its channel 32 in the coupling member. Tightening of the nut 26 therefore secures both the rod 10 and the bone fixation element 12 rigidly to the coupling member 14.

Figures 6A, 6B:
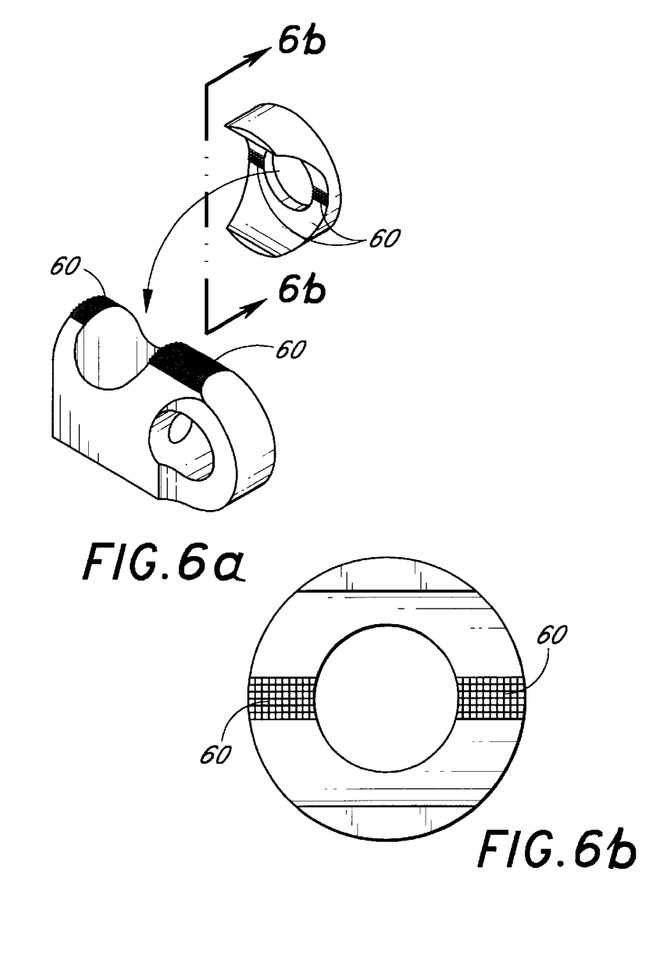
FIG. 6a is a perspective view of the coupling member and the collar member of the fixation system of the present invention, illustrating toothed surfaces on both the coupling member and the collar member.
FIG. 6b is a bottom plan view of the collar member of the fixation system of the present invention of the collar member taken along lines 6b—6b of FIG. 6a, further illustrating a toothed surface on the bottom of the collar.
Figures 7A, 7B:
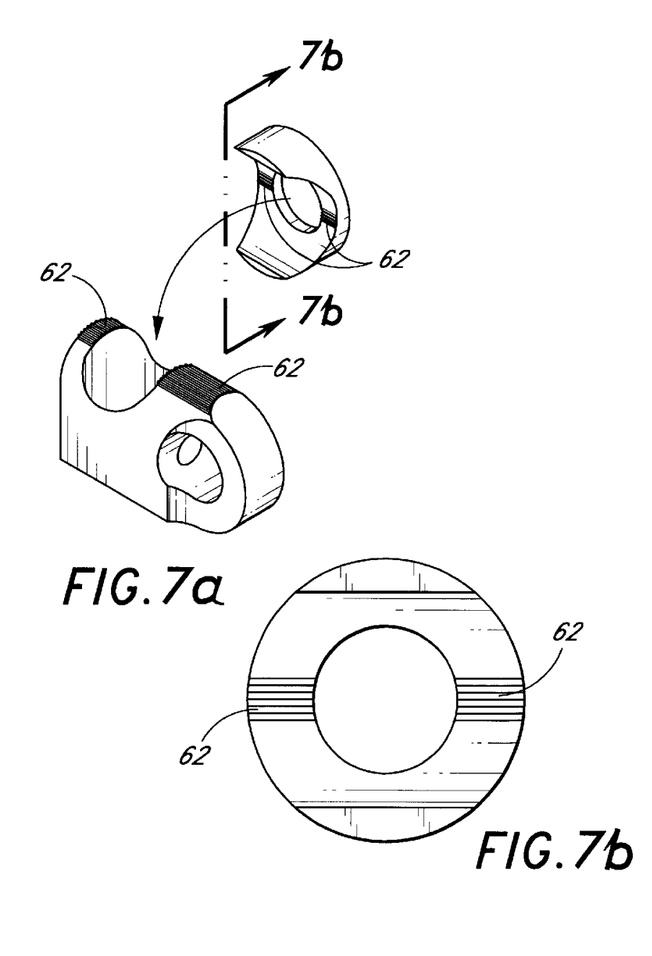
FIG. 7a is a perspective view of the coupling member and the collar member of the fixation system of the present invention, illustrating serrated surfaces on both the coupling member and the collar member.
FIG. 7b is a bottom plan view of the collar member of the fixation system of the present invention, taken along lines 7b—7b of FIG. 7a, further illustrating a serrated surface on the bottom of the collar.

To further facilitate a secure connection between these three elements, the top of the coupling element 14 and the rounded bottom side of the collar 50 are provided with mutually engaging teeth 60, illustrated in FIGS. 6a and 6b, or serrations 62, illustrated in FIGS. 7a and 7b. When the teeth 60 or serrations 62 on the collar member 50 are pressed tightly onto the matching teeth 60 or serrations 62 on the top of the coupling member 14 by tightening the nut 26, slippage and creep over time are essentially eliminated, even at relatively large deviations from perpendicular orientations between the rod 10 and the bone fixation element 12.

The size and depth of the teeth or serrations are not crucial, but they should be small enough so that fine angular adjustment is possible. In one preferred embodiment, the teeth or serrations are 0.007 inches in height, with a 0.014 inch separation between adjacent peaks.

Preferably, all of the components of the fixation system of the present invention are made from titanium or titanium alloy. However, other biocompatible substances such as stainless steel or various biocompatible plastics would also be suitable. Furthermore, numerous variations and modifications of the invention will become readily apparent to those skilled in the art. Accordingly, the scope of the invention should not be construed as limited to the specific embodiment depicted and described but rather, the scope is to be defined by the appended claims and their equivalents.

What is claimed is:

1. A coupler in a spinal fixation system comprising a body having a fixation rod channel therethrough and a bone fixation element channel therethrough, wherein said bone fixation element channel has a first exit opening with a first cross sectional diameter, a second exit opening with a second cross sectional diameter and a minimum cross sectional area at a location within the interior of said bone fixation element channel between said first exit opening and said second exit opening thereby forming an approximately hour glass shaped longitudinal cross section of said bone fixation element channel.

2. The coupler of claim 1, wherein said body additionally has a second channel therethrough.

3. The coupler of claim 2, wherein said second channel has a substantially constant cross sectional area along its longitudinal axis.

4. The coupler of claim 3, wherein said second channel has a substantially circular cross section.

5. A spinal fixation system comprising:

at least one bone fixation element having a first portion adapted for bone engagement, a threaded second portion, and a third portion between said first and second portions defining an outer surface having an approximately circular cross section;

a linking rod having an elongate substantially cylindrical configuration; and a coupler having a body with a first channel therethrough accepting and surrounding a portion of said linking rod and a second channel therethrough accepting and surrounding a portion of said bone fixation element wherein said third portion of said bone fixation element is in contact with said linking rod within said coupler.

6. The spinal fixation system of claim 5 wherein said third portion of said bone fixation element is contoured such that the cross sectional area of said third portion is different in at least two places along said third portion.

7. The spinal fixation system of claim 5, wherein said third portion forms a tapered approximately conical outer surface of said bone fixation element.

8. A spinal fixation system comprising:

a bone fixation element;

an elongate linking member; and, a coupler comprising a body having a first orifice therethrough accepting and surrounding a portion of said elongate linking member and a second orifice therethrough accepting and surrounding a portion of said bone fixation element, said second orifice defining a channel having two ends and a central portion between said two ends, wherein the cross sectional area at said central portion of said channel is smaller than the cross sectional area of either of said two ends.

9. The spinal fixation system of claim 8, wherein said elongate linking member and said bone fixation element are in contact with one another.

10. The spinal fixation system of claim 8, wherein said second orifice has a cross sectional area which is different in at least two locations along its longitudinal axis.

11. The spinal fixation system of claim 10, wherein said elongate linking member and said bone fixation element are in contact with one another.

12. A bone fixation apparatus comprising:

a bone fixation element adapted to engage a portion of a bone, the bone fixation element comprising a bone engagement portion and a load bearing surface;

a linking member adapted to interconnect a plurality of bone fixation elements so as to maintain a desired positional relationship between said plurality of bone fixation elements; and a coupling member having a first channel for receiving a portion of the bone fixation element, and a second channel for receiving a portion of the linking member, wherein the central longitudinal axes of the first and second channels are offset with respect to one another, and wherein said first and second channels are laterally spaced such that intersecting surfaces form a window, so that the load bearing surface of the bone fixation element directly contacts the linking member through said window after axial insertion of the bone fixation element into the second channel, and after axial insertion of the linking member into the first channel, such that an axially directed securing force applied to said bone fixation element so as to draw said bone fixation element further into said first channel, produces a laterally directed securing force between the bone fixation element and the linking member.

* * * * *

UNITED STATES PATENT AND TRADEMARK OFFICE
CERTIFICATE OF CORRECTION

| | | |
|---|---|---|
| PATENT NO. | : 6,030,388 | Page 1 of 1 |
| APPLICATION NO. | : 08/695318 | |
| DATED | : February 29, 2000 | |
| INVENTOR(S) | : Yoshimi et al. | |

It is certified that error appears in the above-identified patent and that said Letters Patent is hereby corrected as shown below:

On title page: (item 63)

Related U.S. Application Data

Continuation of application No. 08/405,813, filed on March 16, 1995, now Patent No. 5,562,661.

Column 1:

This application is a continuation of U.S. Ser. No. 08/405,813, filed March 16, 1995, March 16, 1995, now Patent No. 5,562,661.

Signed and Sealed this

Eighth Day of August, 2006

JON W. DUDAS
*Director of the United States Patent and Trademark Office*